United States Patent
Furey et al.

(10) Patent No.: US 9,867,623 B2
(45) Date of Patent: Jan. 16, 2018

(54) APPARATUS FOR DELIVERING FILAMENTARY MATERIAL INTO A PATIENT

(71) Applicant: Cook Medical Technologies LLC, Bloomington, IN (US)

(72) Inventors: Aidan Furey, Valby (DK); Steen Aggerholm, St. Heddinge (DK); Palle Munk Hansen, Vemmedrup (DK); Anders Ginge Jensen, Hornslet (DK); Kirsten Asser Larsen, Moerkoev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 409 days.

(21) Appl. No.: 14/732,333

(22) Filed: Jun. 5, 2015

(65) Prior Publication Data
US 2015/0351774 A1 Dec. 10, 2015

Related U.S. Application Data

(60) Provisional application No. 62/008,104, filed on Jun. 5, 2014.

(51) Int. Cl.
*A61M 29/00* (2006.01)
*A61B 17/12* (2006.01)
(Continued)

(52) U.S. Cl.
CPC .... *A61B 17/12118* (2013.01); *A61B 17/1214* (2013.01); *A61B 17/12113* (2013.01);
(Continued)

(58) Field of Classification Search
CPC ........ A61B 17/12109; A61B 17/12113; A61B 17/12118; A61B 17/1214;
(Continued)

(56) References Cited

U.S. PATENT DOCUMENTS 5,021,059 A * 6/1991 Kensey .............. A61B 17/0057
604/15
5,263,927 A * 11/1993 Shlain .............. A61B 17/00234
604/13
(Continued)

FOREIGN PATENT DOCUMENTS

EP 0743047 A2 11/1996
EP 2 361 567 A1 6/2011
(Continued)

*Primary Examiner* — Jonathan Miles
*Assistant Examiner* — Wade Miles
(74) *Attorney, Agent, or Firm* — Woodard, Emhardt, Moriatry, McNett & Henry LLP

(57) ABSTRACT

There are disclosed various dispensing mechanisms for dispensing filamentary material (24) through a catheter (12) into a treatment site of a patient, for example into an aneurysm sack (20) in a patient's vessel (22). In one embodiment, the dispensing assembly (30) includes a chamber having a spherical carrier (50) onto which filamentary material (24) is wound. Upon injecting driving fluid into the dispensing assembly (30) filamentary material (24) unwinds from the spherical carrier (50) and is pulled through the catheter (12) to be dispensed from the distal end (18) of the catheter.

25 Claims, 10 Drawing Sheets

(51) Int. Cl.
  *A61B 17/00* (2006.01)
  *A61B 90/00* (2016.01)
(52) U.S. Cl.
  CPC .............. *A61B 2017/00004* (2013.01); *A61B 2017/00539* (2013.01); *A61B 2017/00907* (2013.01); *A61B 2017/1205* (2013.01); *A61B 2090/032* (2016.02)
(58) Field of Classification Search
  CPC .......... A61B 17/12145; A61B 17/1215; A61B 17/12154; A61B 2017/00535; A61B 2017/00539; A61M 25/09041
  See application file for complete search history.

(56) References Cited

U.S. PATENT DOCUMENTS

| | | | |
|---|---|---|---|
| 5,911,731 A | 6/1999 | Pham et al. | |
| 6,093,179 A * | 7/2000 | O'Hara | A61B 17/3415 604/159 |
| 6,296,632 B1 * | 10/2001 | Luscher | A61B 17/12022 604/264 |
| 6,299,590 B1 | 10/2001 | Luscher et al. | |
| 6,312,421 B1 | 11/2001 | Boock | |
| 6,440,098 B1 | 8/2002 | Luscher | |
| 6,589,199 B1 | 7/2003 | McCrory et al. | |
| 6,629,947 B1 | 10/2003 | Sahatjian et al. | |
| 2003/0036712 A1 * | 2/2003 | Heh | A61M 25/09041 600/585 |
| 2005/0033323 A1 | 2/2005 | Kim | |
| 2006/0147483 A1 | 7/2006 | Chaouk et al. | |
| 2010/0042117 A1 | 2/2010 | Kim et al. | |
| 2014/0148791 A1 | 5/2014 | Barker et al. | |
| 2015/0351773 A1 * | 12/2015 | Furey | A61B 17/12113 606/200 |
| 2017/0100129 A1 * | 4/2017 | Furey | A61B 17/12186 |

FOREIGN PATENT DOCUMENTS

| | | |
|---|---|---|
| WO | WO 1996/004954 A1 | 2/1996 |
| WO | WO 1999/011191 A1 | 3/1999 |
| WO | WO 1999/11191 A1 | 3/1999 |
| WO | WO 2004/098420 A2 | 11/2004 |

* cited by examiner

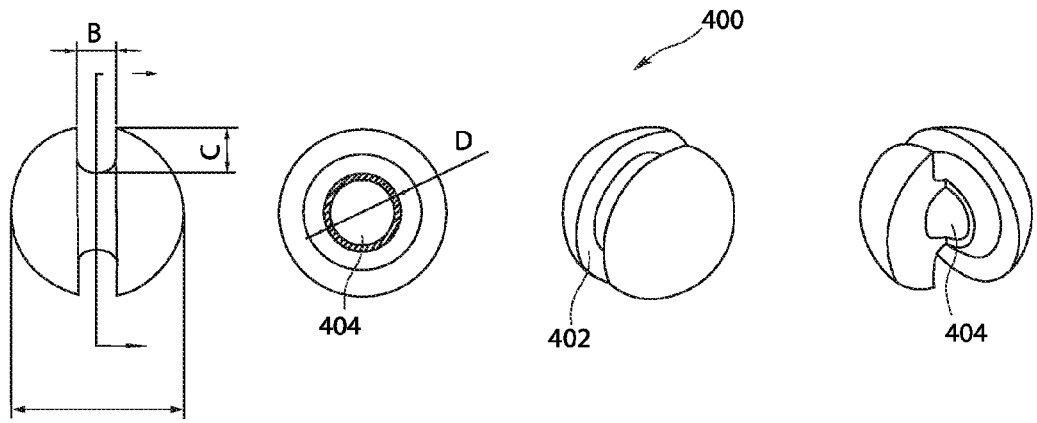
Fig. 6
| Part # | ØA | B | C | ØD |
|---|---|---|---|---|
| B01 | 12.5 | 3 | 3 | 4 |
| B02 | 13.5 | 3 | 3.5 | 5 |
| B03 | 26 | 3 | 5 | 15 |
| B04 | 27 | 3 | 5 | 15 |
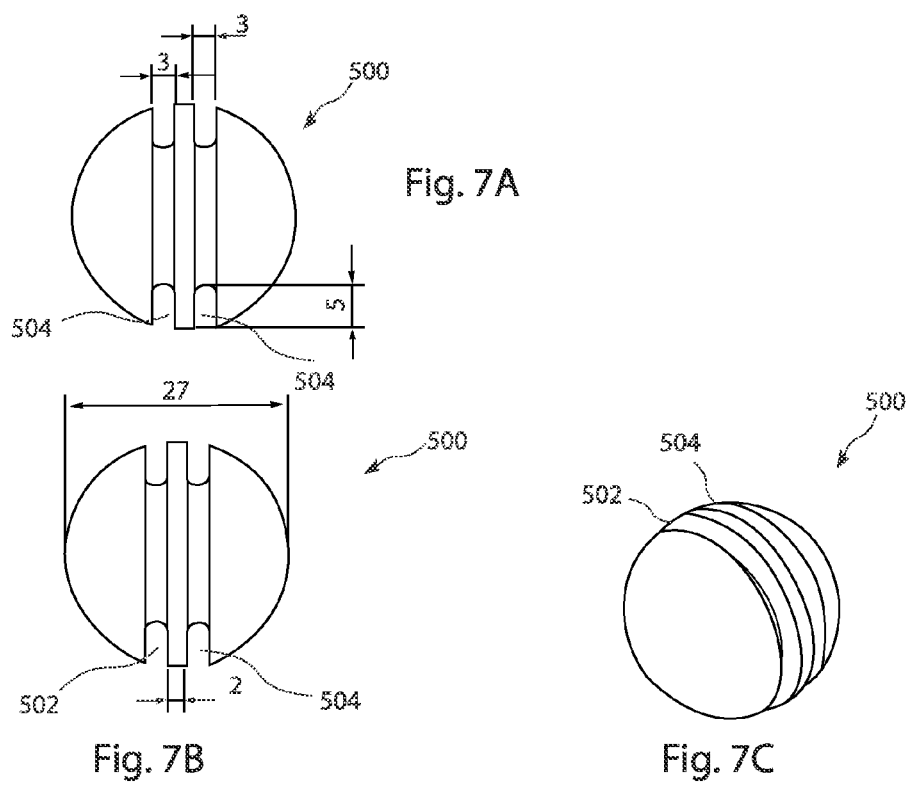
Fig. 7A
Fig. 7B
Fig. 7C

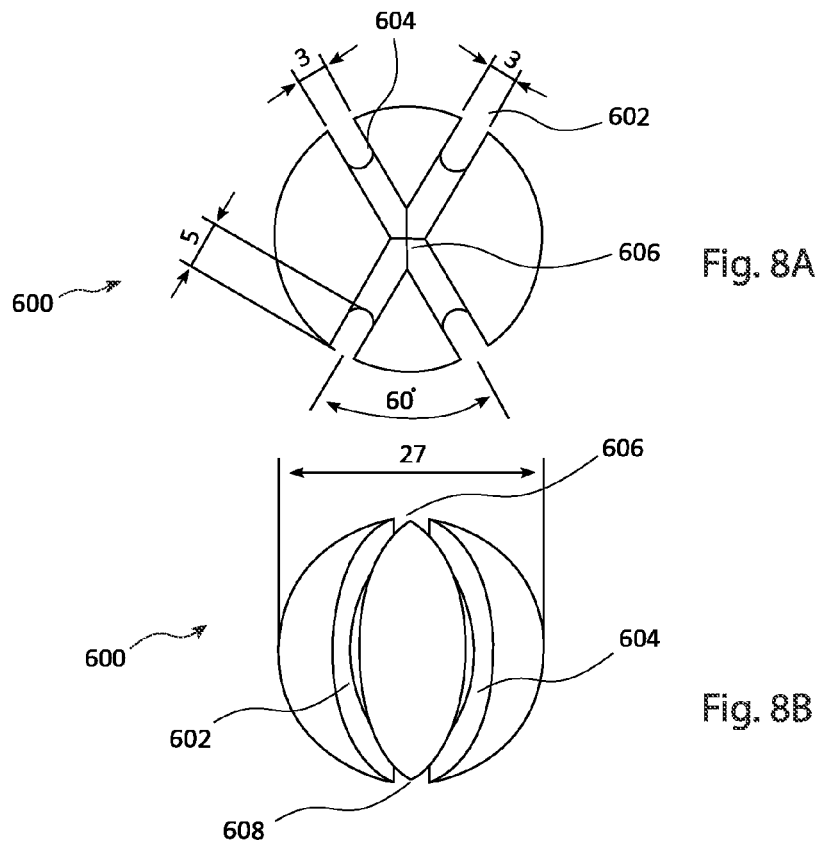
Fig. 8A
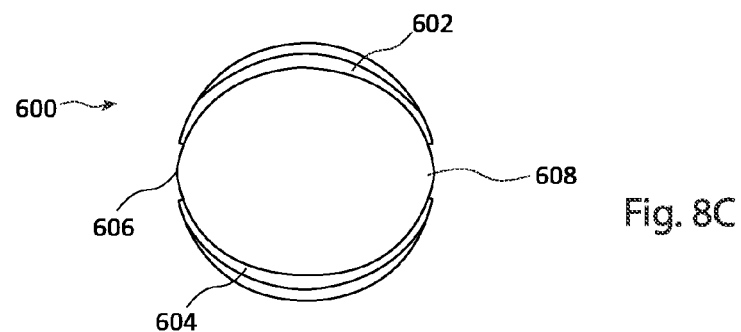
Fig. 8B
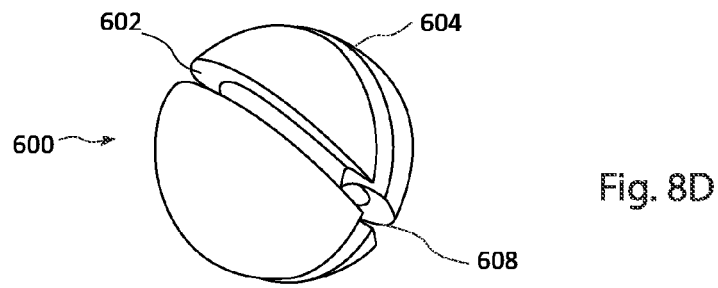
Fig. 8C
Fig. 8D

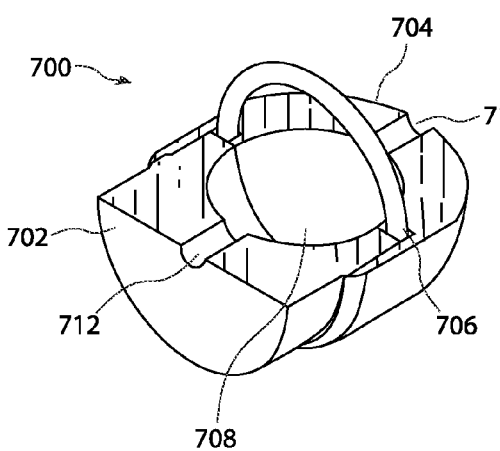
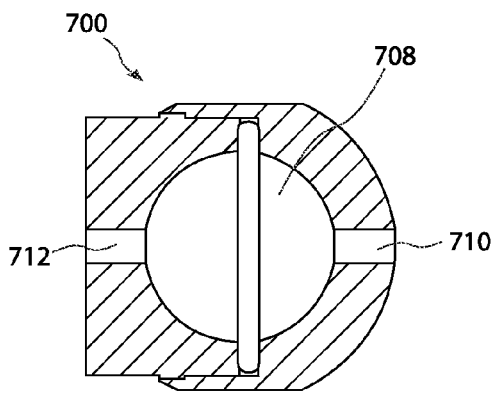
Fig. 9A
Fig. 9B
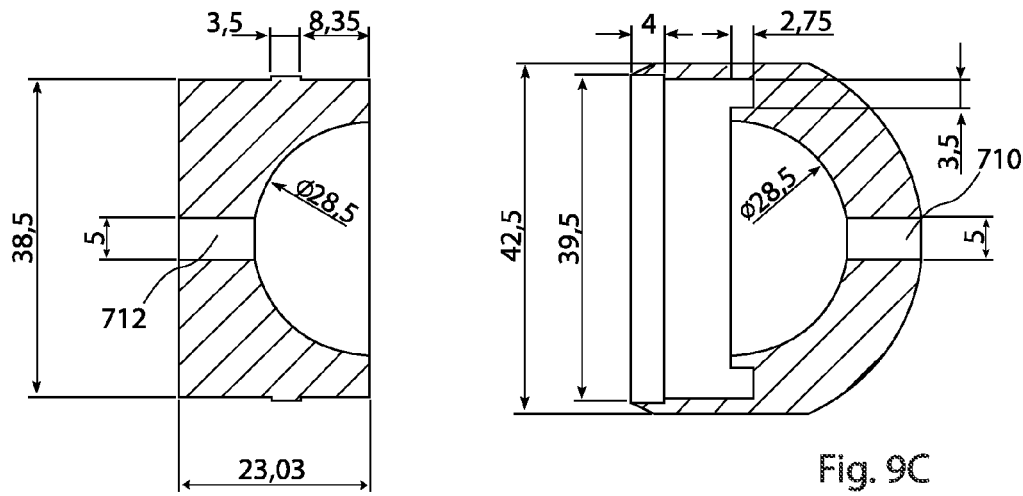
Fig. 9C
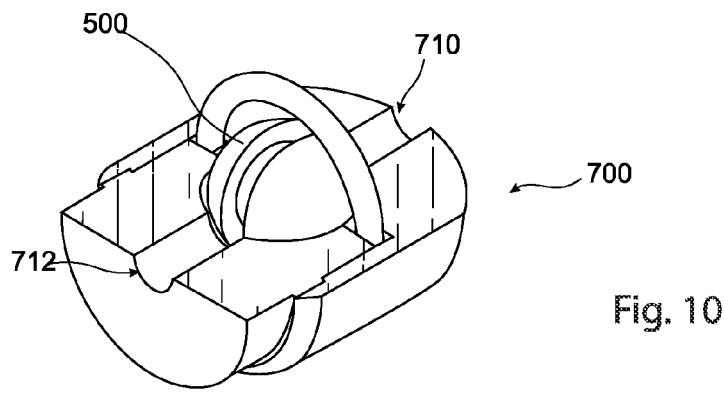
Fig. 10

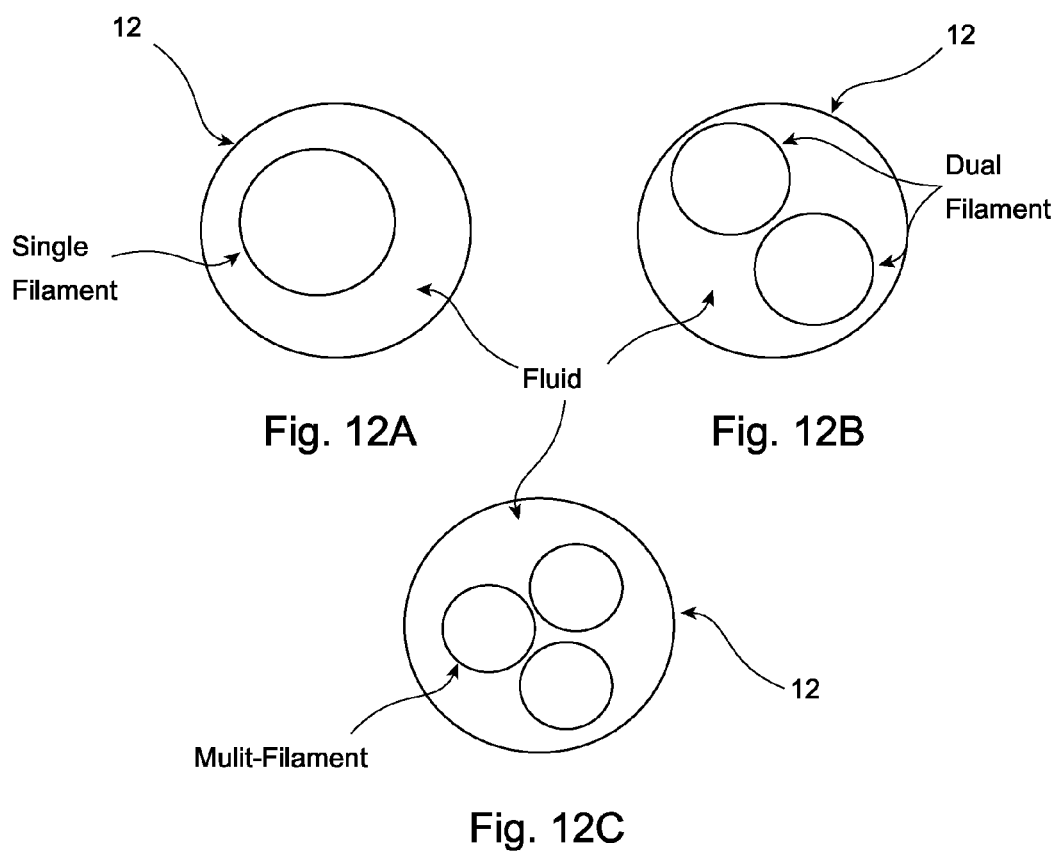

APPARATUS FOR DELIVERING FILAMENTARY MATERIAL INTO A PATIENT

REFERENCE TO RELATED APPLICATION

This application claims the benefit of U.S. Provisional Patent Application No. 62/008,104, filed Jun. 5, 2014, which is hereby incorporated by reference.

TECHNICAL FIELD

The present invention relates to apparatus and a method for delivering filamentary material into a patient, in the preferred embodiments to delivery of material endoluminally through a percutaneous entry point. The preferred embodiments can be used for filling an aneurysm, for closing a vessel or other organ, as well as for other medical treatments.

BACKGROUND ART

There are several medical conditions which can benefit from implantation into a patient of a filler material, an embolization or other device, whether temporary or permanent. Examples include the closure of blood vessels or other lumens so as to occlude these. Another example for which such procedures can be particularly useful is in the treatment of aneurysms, where a part of a vessel wall weakens and then expands outwardly to create an enlarged zone of the vessel, often having the form of a sac. This vessel expansion occurs as a result of blood pressure and tends to continue due to further and progressive weakening of the vessel wall. If left untreated, persistent pressure from the blood flow on the weakened wall tissue can lead to eventual rupture of the vessel and consequential haemorrhaging. Treatments for aneurysms have therefore focused on reducing the pressure on the weakened vessel wall, for instance by diverting blood flow or by isolating the weakened vessel wall, for instance by means of a stent graft. Another treatment method involves filling the aneurysm sac with a filler material which stops the flow of blood into the sac and therefore stops or substantially reduces the pressure on the weakened walls. The filler may be an embolization coil, which will cause blood therearound to clot and thus close the sac and provide a protective barrier to prevent vessel rupture. In other instances, the aneurysm may be filled with a biocompatible material, such as a hydrogel or a polysaccharide fibre, which may be of a biodegradable nature. A biodegradable filler performs the same function as an embolization coil, that is to fill the aneurysm sac and provide pressure protection to the weakened vessel walls, with the additional advantage of allowing remodeling of the vessel wall over time. Moreover, biodegradation of the filler will ensure that no foreign matter remains in the patient's vessel after conclusion of the treatment.

Such fillers and coils can also be used to close off a vessel or other lumen in a patient.

The process of introducing such a filler or coil into a patient can take time, particularly given that this is often carried out remotely from the aneurysm by an endoluminal procedure.

Examples of prior art devices and methods can, for instance, be found in U.S. Pat. No. 6,312,421, US-2006/0147483, U.S. Pat. No. 6,589,199, U.S. Pat. No. 6,440,098.

SUMMARY

The present invention seeks to provide an improved apparatus for delivering filamentary material into a patient and in the preferred embodiments into a vessel or aneurysm sac.

According to an aspect of the present invention, there is provided apparatus for delivering filamentary material into a patient including: a tubular delivery element having a proximal end, a distal end and a lumen extending within the tubular delivery element from the proximal to the distal ends; a material dispenser coupled at the proximal end of the tubular delivery element, the material dispenser including a receptacle having an internal wall of which at least a part has a generally rounded shape, the receptacle including an aperture for receiving driving fluid into the receptacle and an outlet coupled to the lumen of the tubular delivery element; and a material carrier operable to carry a length of filamentary material, the material carrier having a generally rounded shape conforming at least to said rounded part of the internal wall of the receptacle and having a size smaller than a size of the receptacle; the filamentary material being wound around the carrier and having an end located through the outlet for feeding into and through the lumen of the tubular delivery element.

The tubular delivery element may be or may include at least one of a catheter, a cannula and a needle.

Providing the material on a carrier having a rounded form can enable rapid dispensing of the material and as a result a more rapid medical procedure. Moreover, there is less risk of filamentary material snagging during the dispensing process.

It is to be understood that references to a rounded carrier, or ovoidal or spherical carrier are not intended to limit the disclosure to precise spheres as the carrier could have any form approaching the shape of a sphere or ovoid.

Preferably, the carrier is free rotate in any direction within the receptacle.

In the preferred embodiments, the carrier includes at least one groove extending therearound, filamentary material being retained in the groove. Advantageously, the at least one groove is disposed at or adjacent a point of greatest diameter or perimeter of the carrier.

In an embodiment, the carrier includes a plurality of grooves. These may lie in substantially or precisely parallel planes relative to one another, while in some embodiments the or at least two of the grooves lie in planes which cross one another.

Advantageously, the carrier is made of a plastics material. The carrier may include a hollow core. It is preferred that the carrier is made of a material buoyant in water or a water based solution. In any and all of these embodiments, the carrier can in practice float within the receptacle when the receptacle is filled with driving fluid, which considerably facilitates the dispensing operation by reducing friction. In other words, the carrier is preferably designed to be suspended in fluid during the dispensing operation.

It is preferred that the carrier is free to rotate in any direction within the receptacle. In other words, it is preferred that the carrier is unattached or uncoupled from the receptacle or any part of the receptacle.

The receptacle is preferably at least partially transparent or translucent, in some embodiments being substantially or entirely transparent or translucent.

The apparatus may include a fluid supply and pump for pumping driving fluid into the receptacle. The pump may include a syringe.

The filamentary material could be of any type deemed suitable for performing a medical function and could be sub intestine submucosa (SIS), polysaccharide, a biocompatible polymeric thread or other biocompatible material. Specific examples, though the disclosure herein is not limited to these, include: woven polyester (e.g. DACRON®), polyamide (e.g. Nylon), expanded polytetrafluoroethylene (ePTFE; e.g. GORE-TEX®); bioremodelable materials such as: extracellular matrix material (ECM) for instance submucosa, renal capsule membrane, dermal collagen, dura mater, pericardium, fascia lata, serosa, peritoneum and basement membrane layers. Examples of submucosa include: intestinal submucosa, including small intestinal submucosa, stomach submucosa, urinary bladder submucosa and uterine submucosa.

According to another aspect of the present invention, there is provided a filamentary material carrier for apparatus for delivering filamentary material into a patient, the material carrier being designed to carry a length of filamentary material and having a generally rounded shape; the filamentary material being wound around the carrier and in practice having an end located though the outlet of a receptacle for feeding into and through the lumen of an attached catheter.

The carrier may have any of the features and elements disclosed herein.

According to another aspect of the present invention, there is provided apparatus for delivering filamentary material into a patient, including a receptacle provided with an internal chamber for holding filamentary material, an aperture for receiving driving fluid into the chamber, an outlet through which filamentary material can pass from the chamber, and a pressure sensitive valve associated with the receptacle, the pressure sensitive valve being closed when the pressure of driving fluid is below a threshold and open when the pressure of driving fluid is above the threshold, the pressure sensitive valve when open allowing fluid flow through the chamber and dispensation of filamentary material from the outlet.

The pressure sensitive valve can ensure that driving fluid is supplied at a sufficient pressure to drive filamentary material through the catheter with minimal use of driving fluid.

Advantageously, the valve is located at the inlet.

In an embodiment, the valve includes at least one resilient valve leaf, deformable when fluid pressure thereon exceeds the threshold.

Preferably, the valve is domed, which enables it to allow one-way fluid flow therethrough.

Other features of the apparatus and method disclosed herein will become apparent from the following specific description of preferred embodiments.

BRIEF DESCRIPTION OF THE DRAWINGS

Embodiments of the present invention are described below, by way of example only, with reference to the accompanying drawings, in which:

FIG. 6 shows the carrier of FIGS. 5A to 5B with a table of indicative dimensions;

FIGS. 7A to 7C show another embodiment of spherical material carrier;

FIGS. 8A to 8D show a further embodiment of spherical material carrier;

FIGS. 9A to 9C are cross-sectional views of another embodiment of chamber for holding a spherical material carrier;

FIG. 10 is a part cut-away view of the chamber of FIGS. 9A to 9C with a spherical carrier held therein;

FIGS. 12A to 12C show in schematic form a catheter in transverse cross-section with one or more filaments of bioabsorbable material held therein;

DETAILED DESCRIPTION

There are described below various embodiments of apparatus for feeding filamentary material into a patient. The teachings herein are particularly useful for feeding blocking material into an aneurysm sac of a weakened vessel, so as to close off the aneurysm sac to blood flow and blood pressure. The apparatus can also be used to supply material to occlude a vessel, for example. The material can be of a type which permanently remains in the patient, thus as a permanent closure or occlusion device, or may be bioresorbable or biodegradable, allowing tissue remodeling over time. In the case of aneurysm treatment, once pressure is removed from within the aneurysm sac the weakened wall tissue can remodel and often will heal fully. In such cases, it is not necessary to maintain a sac filler.

Figure 1:
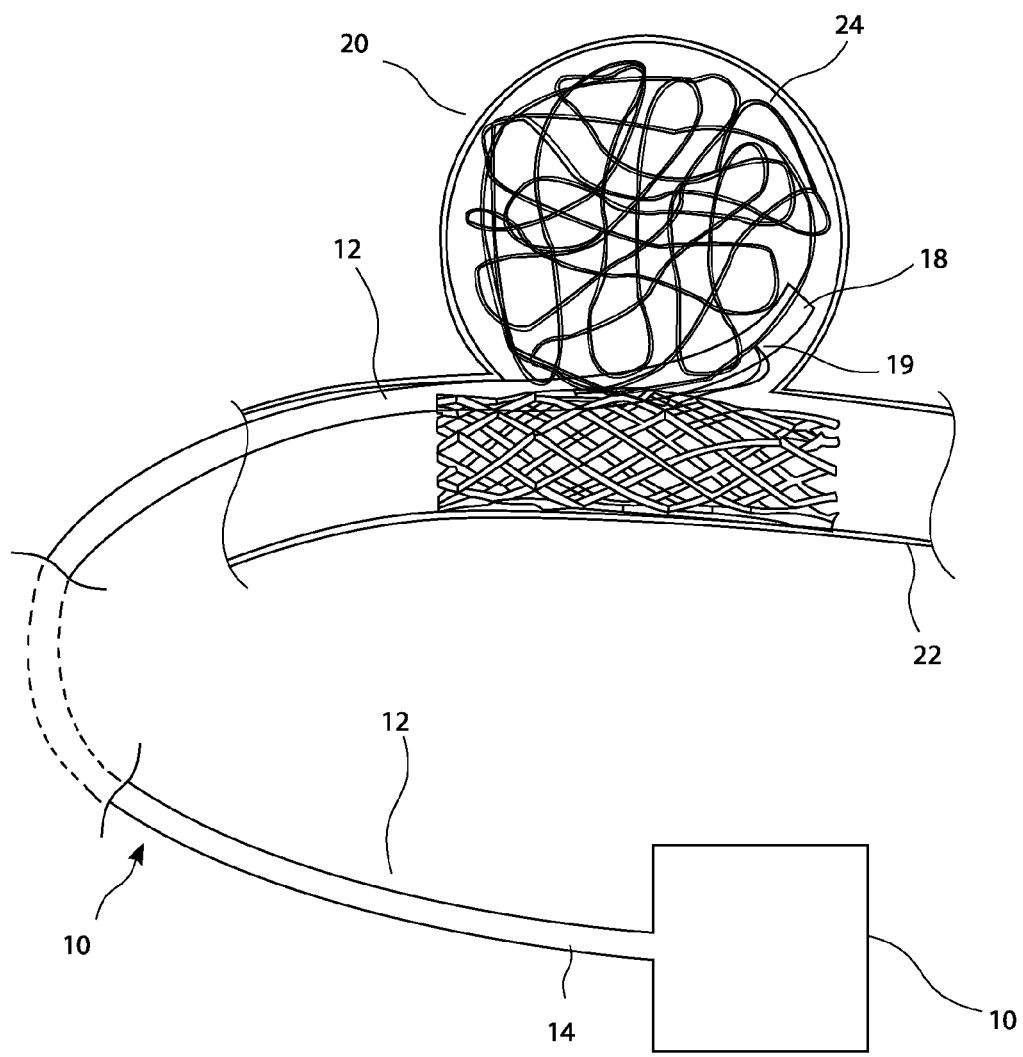
FIG. 1 is a schematic diagram of an embodiment of material feed apparatus according to an embodiment of the invention.

Referring to FIG. 1, there is shown in schematic form a material dispensing assembly 10 incorporating the features of the embodiments disclosed herein. The dispensing assembly 10 includes in this embodiment a catheter 12 having a proximal end 14 coupled to a material receptacle 16, described in further detail below, and a distal end 18 which is passed endoluminally through the vasculature of the patient up to the treatment site, into the sack 20 of an aneurysm formed in a blood vessel 22. The apparatus 10 is designed to dispense into the aneurysm sack 20 filamentary material 24 from the material receptacle 16 through the lumen of the catheter 12. The material dispensed can be any biocompatible material including biocompatible polymeric thread, polysaccharide or other suitable material. The preferred filamentary material also includes SIS (small intestine submucosa). Specific examples, though the disclosure herein is not limited to these, include: woven polyester (e.g. DACRON®), polyamide (e.g. Nylon), expanded polytetrafluoroethylene (ePTFE; e.g. GORE-TEX®); bioremodelable materials such as: extracellular matrix material (ECM) for instance submucosa, renal capsule membrane, dermal collagen, dura mater, pericardium, fascia lata, serosa, peritoneum and basement membrane layers. Examples of submucosa include: intestinal submucosa, including small intestinal submucosa, stomach submucosa, urinary bladder submucosa and uterine submucosa.

The distal end of the catheter 12 is typically fed into the aneurysm sac through a stent 19, which may be a braided stent or any other known stent structure. The stent 19 not only positions the distal end 18 of the catheter but also holds the filamentary material in position.

The filamentary material 24 is intended to fill at least a significant part of the volume of the aneurysm sack 20 so as to stop the flow of blood into the aneurysm 20 and as a result reduce the pressure of blood on the weakened vessel walls of the aneurysm. In the case of a bioresorbable or bioabsorbable material, this will eventually be resorbed or absorbed, typically after a sufficient period which allows recovery of the weakened vessel wall and remodeling of the vessel. In other cases the fibrous material remains permanently within the aneurysm sack, effectively closing this off.

The fibrous material is typically provided as a thin thread or element, for which a substantial length is dispensed from the distal end 18 of the catheter 12 into the aneurysm sack 20 during a deployment procedure. For this purpose, and as described below, the material receptacle 16 includes substantial lengths of filamentary material and held within the material receptacle 16 in such a manner that the material can be reliably and quickly dispensed from the receptacle 16 to the distal end 18 of the catheter 12 and into the treatment site.

It is to be understood that the device 10 shown in FIG. 1 could be used in other medical procedures, including, for example, for occlusion of blood vessels, for delivery of filamentary material for other medical applications.

Figure 2:
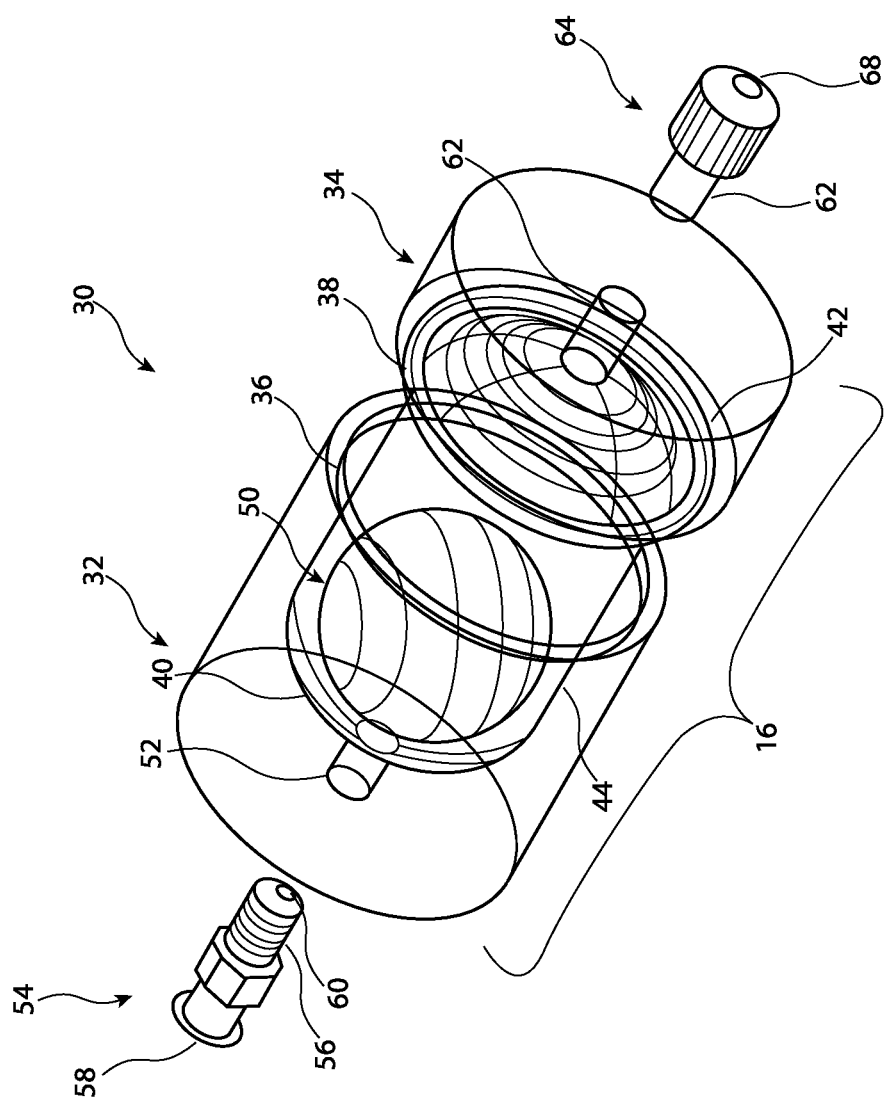
FIG. 2 is an exploded view of an embodiment of material receptacle and dispensing element for the apparatus of FIG. 1.
Figure 3:
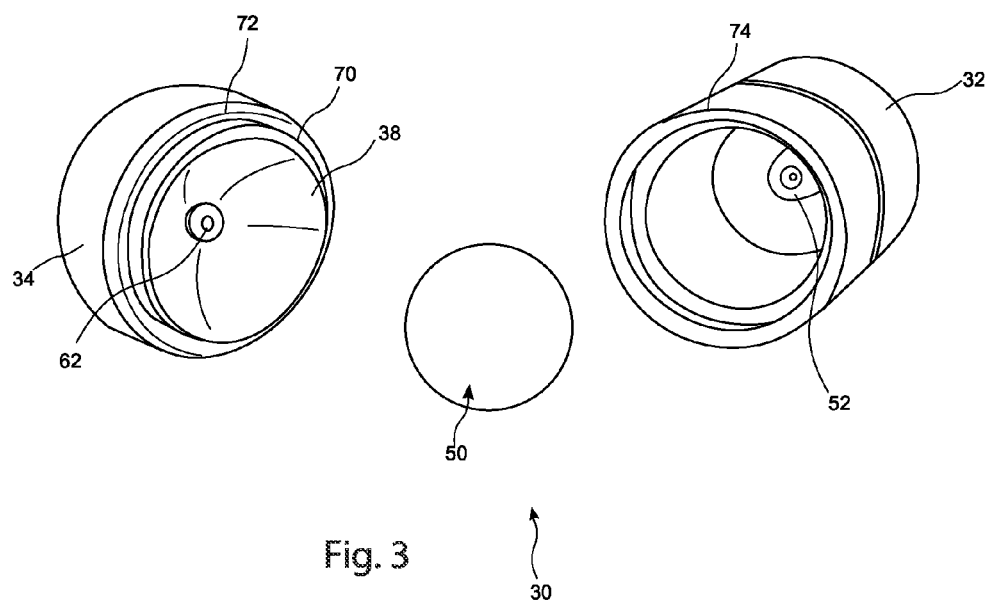
FIG. 3 is a view of the principal components of the material receptacle and dispensing element of FIG. 2.
Figure 4:
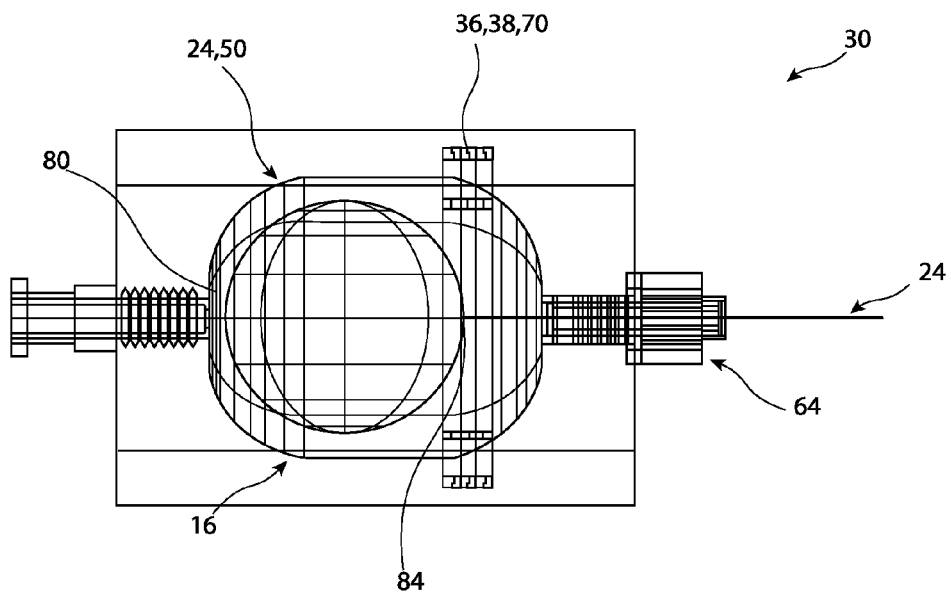
FIG. 4 is a side elevational view of the material receptacle and dispensing element of FIG. 2 in assembled form.

FIGS. 2 to 4 show an embodiment of material dispensing assembly 30 which can be used as the material receptacle 16 of FIG. 1.

Referring first to FIG. 2, this shows the principal components of a dispensing assembly 30 which can be used as the receptacle 16 in FIG. 1. The dispensing assembly 30 is formed of first and second parts 32, 34 which are coupled together, in this embodiment, by means of cooperating female and male threaded connections 36, 38 respectively. The receptacle 16 formed by the first and second parts 32, 34 has, in this embodiment, a generally cylindrical outer form and provides an internal surface 40, 42 which is at least part spherical. In this particular embodiment, the internal wall 40 has a part spherical base and a cylindrical intermediate section 44, while the internal wall part 42 is part spherical. Thus, when the two receptacle parts 32, 34 are coupled together, the internal wall has a cylindrical internal wall portion 44 bounded either end by the part spherical walls 40, 42.

Disposed within the receptacle 16 is a generally spherical material carrier or ball 50, around which filamentary material can be wrapped as explained below. The spherical carrier 50 has a diameter significantly less than the diameter of the chamber formed by the walls 40-44, such that the spherical carrier 50 can roll generally unhindered within the chamber even when the spherical carrier is loaded with filamentary material. The cylindrical portion 44 of the internal wall of the receptacle 16 enables the spherical carrier 50 to reciprocate backwards and forwards within the receptacle as filamentary material unwinds from the spherical carrier 50, which can substantially facilitate the unwinding process.

The first receptacle part 32 includes an inlet 52 which in this embodiment has an internal screw thread matched to an external screw thread 56 of a male element of a first luer lock connector 54. The connector 54 also includes a luer fitting 58 of conventional form and is provided with an conduit or bore 60 therethrough. The connector 54 and inlet 52 are used for supplying driving fluid into the receptacle 16, for use in pulling the filamentary material from the carrier 50 through the device and catheter, as described in further detail below.

The receptacle part 34 includes an outlet 62 which is similarly provided with an internal screw thread for coupling to a male threaded connector part 66 of a second luer fitting 64, again of conventional form. The second luer fitting 64 is selected to fit onto a corresponding luer connector at the proximal end 14 of a catheter 12. The connector 64 has a bore or conduit 68 therethrough and in practice provides a passage from the chamber of the material receptacle 16 and, as described in detail below, an outlet for the filamentary material.

Referring now to FIG. 3, this shows in better detail some of the components of the assembly 30. In particular, the inlet 52 and outlet 62 in the casing parts 32 and 34 can be seen in better detail. There can also be seen an O-ring seal 70 fitted to the casing part 34 adjacent the threaded male connector element 38. The seal 70 abuts against a radial flange 72 of the part 34 and in practice will also press against the radial end wall 74 of the first receptacle part 32, in practice creating an airtight seal between the two parts and as a result sealing the chamber formed by the internal walls 40-44, apart from through the inlet and outlet 52, 62. The spherical carrier 50 is, in the embodiment of FIG. 3, precisely spherical although this need not necessarily be so as it could in other embodiments be of other generally rounded shape including oval. The carrier 50 may also include (not shown) one or more features for grasping an end of filamentary material, although this is not essential.

Referring now to FIG. 4, this shows the assembly of FIGS. 2 and 3 when assembled, where it can be seen that the spherical carrier 50 is housed within the chamber of the receptacle 10. The spherical carrier 50 has wrapped therearound filamentary material 80, which in this embodiment is wrapped between opposing poles 82, 84 or the spherical carrier 50 and in different radial orientations, such that the filamentary material 80 passes from one pole 82 to the other and back again. An end of the filamentary, that is the outermost end of the material, passes through the outlet 62, through the connector element 62 and in practice into the catheter 12 of the assembly 10. Wrapping the filamentary material 80 in this manner on the spherical carrier 50 will in practice cause the spherical carrier to roll in the same direction during unwinding of the filamentary material 80, with the regular rolling motion being able to create rolling momentum which will assist in the dispensation of filamentary material 80 through the attached catheter 12.

In use, the connector 56 is coupled to a source of driving fluid, typically saline solution, which is pumped into the chamber of the receptacle 16. In its simplest form, the assembly could include a syringe which acts as the source of driving fluid and as the pump. When driving fluid is pumped into the chamber of the receptacle 16, the fluid will flow to and through the outlet 62, which generates a force pulling the filamentary material through the outlet and along the catheter 12 until this reaches the distal end 18, whereupon the filamentary material will be ejected from the catheter and into the treatment site, in the example into the aneurysm sack 20. The driving fluid, in this case saline solution, will be dispersed within the blood stream and play no further part in the delivery process.

In some embodiments, the assembly may hold a length of filamentary material which is sufficient for filling the volume of the aneurysm sack 20, determined prior to the medical procedure for example by standard imaging techniques. In other embodiments, the assembly may be loaded with excess filamentary material 24, in which case the assembly is provided with a cutting element (not shown) disposed to cut the filamentary material once it has been decided that sufficient volume has been dispensed into the treatment site. A cutting element may be located at the distal end 18 of the catheter 12 or at the proximal end 14. The person skilled in the art will be able to appreciate suitable structures for such a cutting element having regard to common general knowledge.

Figure 5A:
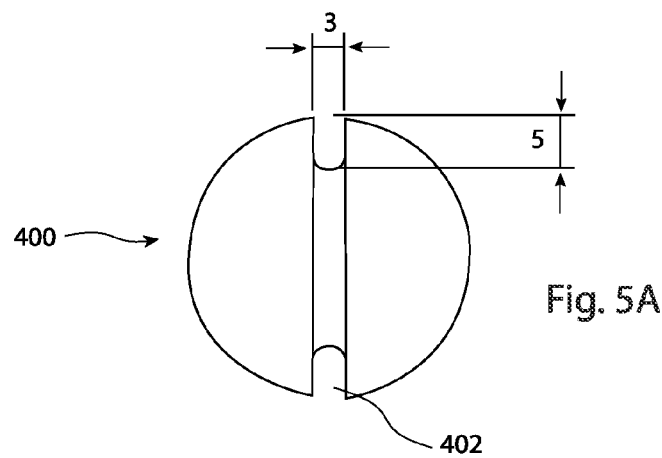
FIGS. 5A to 5D show another embodiment of spherical carrier for carrying and dispensing filamentary material through a delivery catheter.
Figure 5B:
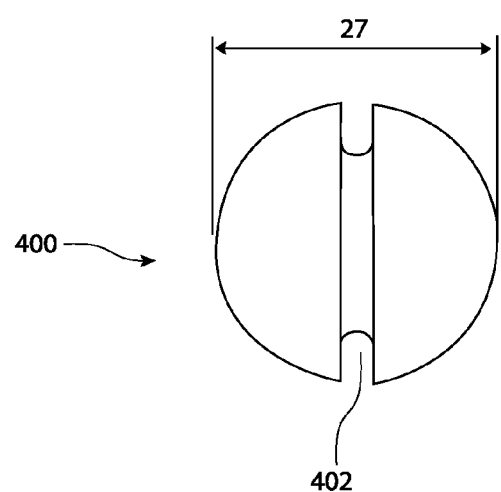
Figure 5C:
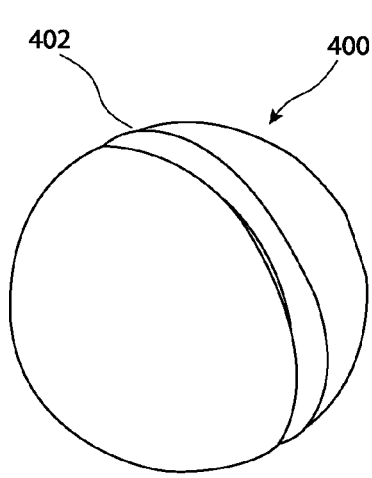
Figure 5D:
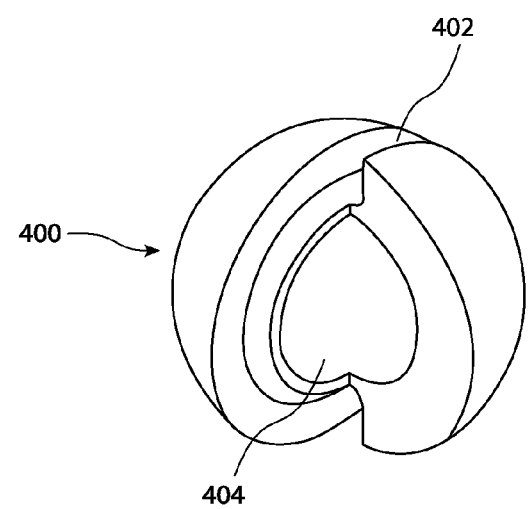

Referring first to FIGS. 5A to 5D, these show another embodiment of spherical carrier 400 which can be used as replacement to the spherical carrier shown in the embodiments of FIGS. 2 to 4. The spherical carrier 400 is preferably made of a lightweight plastics material of low friction and in this embodiment is provided with a groove 402 which extends circumferentially around the carrier 400 about its centre point. In this example, the spherical carrier 400 has a diameter of around 27 mm, for location within a holder having a chamber with an internal diameter of around 28 to 30 mm, while the groove 402 has a width of around 3 mm and a maximum depth of around 5 mm. As can be seen in FIG. 5D, in this embodiment the carrier has a hollow core 404, which provides buoyancy of the carrier in operation, as will be described below. It is to be appreciated that the carrier 400 may be made of a naturally buoyant material, in which case it is not necessary to have a central cavity.

In addition to giving the carrier 400 buoyancy, the central cavity reduces the weight of the carrier, which is considered advantageous as this reduces the momentum of the carrier, which reduces the force required to unwrap filamentary material from the carrier and also reduces the amount of time taken for the carrier 400 to stop rotating upon removal of driving fluid in the device. This explained in further detail below.

The groove 402 is sized so as to be able to accommodate within the volume of the groove the entire volume of filamentary material which is to be delivered by the apparatus. In the preferred embodiment, therefore, the groove 402 is deep and wide enough to ensure that the volume of filamentary material held within the groove 402 does not extend beyond the spherical perimeter of the carrier 400.

It will be appreciated that with filamentary material wound into and along the groove 402, the spherical carrier 400 will in practice rotate in a single direction during unwinding of the filamentary material from the carrier 400.

Referring to FIG. 6, this shows the carrier 400 of FIGS. 5A to 5D alongside a table showing indicative dimensions for different sizes of carrier 400. It has been found that the internal cavity 404 need not have a diameter of greater than around 15 mm for any practical size of carrier 400. The skilled person will appreciate that the values given in FIG. 6 and elsewhere in this description are merely indicative and that the size of the carrier, as well as of the groove or groves and internal cavity, may be different for different applications, lengths of filamentary material to be held by the carrier and the material used to make the carrier itself.

Referring now to FIGS. 7A to 7C, these show another embodiment of spherical carrier 500 having characteristics very similar to the spherical carrier 400 of FIGS. 5A to 6. The spherical carrier 500 may, therefore, also include an internal cavity such as cavity 404 of the embodiment of FIGS. 5A to 6 and be made of the same materials. In the embodiment of FIGS. 7A to 7C, the spherical carrier 500 has a plurality of grooves 502, 504 which are disposed in parallel planes relative to one another, as will be apparent from FIGS. 7A to 7C. Again, the dimensions, which are in millimetres, are for indicative purposes only, for a particular size of carrier and housing. Similarly, the grooves 502, 504 are sized to hold the entire volume of filamentary material wrapped thereinto.

The structure of FIG. 7A to 7C enables, in this example, two lengths of filamentary material to be held in the carrier 500 and in practice to be dispensed together as a multiple filament. This is useful for larger aneurysms, such as aneurysms occurring in the ascending abdominal aorta (AAA) and other primary vessels. It is to be appreciated that a spherical carrier similar to that of the embodiment of FIGS. 7A to 7C could include more than two parallel grooves. It will be appreciated also that for a greater number of grooves, the spherical carrier may have a greater diameter.

FIGS. 8A to 8D shows another embodiment of spherical carrier 600 similar to the embodiments of FIGS. 5A to 7C and having similar characteristics, including as appropriate an internal cavity (not shown in the drawings). In this embodiment, the spherical carrier 600 includes two grooves 602, 604 therein, which instead of being parallel to one another as in the embodiment in FIG. 7A to 7C, intersect at two diametrically opposing crossing points 606, 608. The grooves 602, 604 are arranged such that a length of filamentary material can be wound in one of the grooves 602 and then in the other groove 604. The manner of winding can involve either winding half of the filamentary material in one go into one of the grooves 602 and the other half in the other groove also in one go (or other proportion which is desired). Another possibility winds a single turn in groove 602 and them a single turn in groove 604, and then back and forth between the grooves 602 and 604 until the entire length of thread has been wound on the carrier 600. Interleaving of the thread windings in this manner could be either in single windings or multiple windings.

This arrangement of grooves 602, 604 will cause the carrier to rotate laterally during the unwinding operation rather than rotating always in the same direction throughout the unwinding operation. This lateral rotation can be advantageous in some circumstances, as well as in reducing unwinding drag potentially caused by embedding of one thread turn into other thread turns located in the groove. It should be pointed out, however, that the inventors have not experienced any incidents of embedding of turns of thread into one another during development of this device.

Referring now to FIGS. 9A to 9C these show another embodiment of casing or holder 700 for use with a spherical carrier as taught herein. The casing, as with previous embodiments, is formed of two parts 702, 704 which interengage, held together by a screw threaded or bayonet fitting for example, and sealed by an O-ring seal 706. The casing 700 provides, in this example, a spherical internal chamber 708 which is preferably only slightly larger than the diameter of the spherical carrier to be held in the cavity 708. The dimensions given in FIG. 9C are indicative dimensions, for a carrier having a diameter of around 27 mm, such that the carrier is a snug fit within the chamber 708. As described above, the chamber 708 preferably has a diameter no more than around 10% greater than the diameter of the spherical carrier. Tighter tolerances are preferred as this minimises any off-axis movement of the carrier within the chamber and also the amount of fluid which is required to operate the device.

The holder 700 includes, as with previously described embodiments, an inlet 710 and an outlet 712, which may have internal threads for coupling to a connector such as a luer connector, for attachment to a source of driving fluid and also to the delivery catheter, respectively.

When the chamber 708 is filled with fluid, the carrier preferably floats within the chamber as a result of its buoyancy, which minimises the rolling friction of the carrier and thereby reduces any unwinding friction of the carrier. In other words, the carrier is preferably designed to be suspended in fluid during the dispensing operation. Furthermore, the provision of only a small amount of fluid between the carrier and the inner wall of the chamber can act solely as lubrication and can assist in the rapid stopping of the carrier once driving fluid is stopped.

Figure 11A:
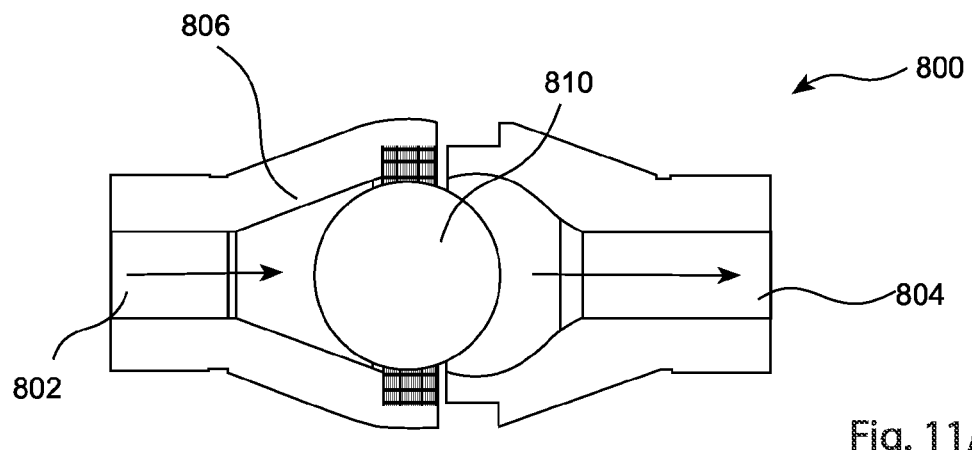
FIGS. 11A to 11C show, in cross-section, another embodiment of chamber for holding a material carrier.
Figure 11B:
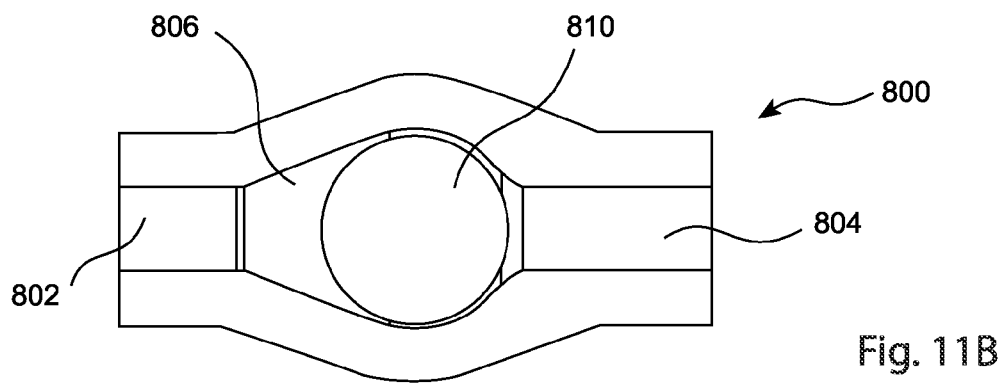
Figure 11C:
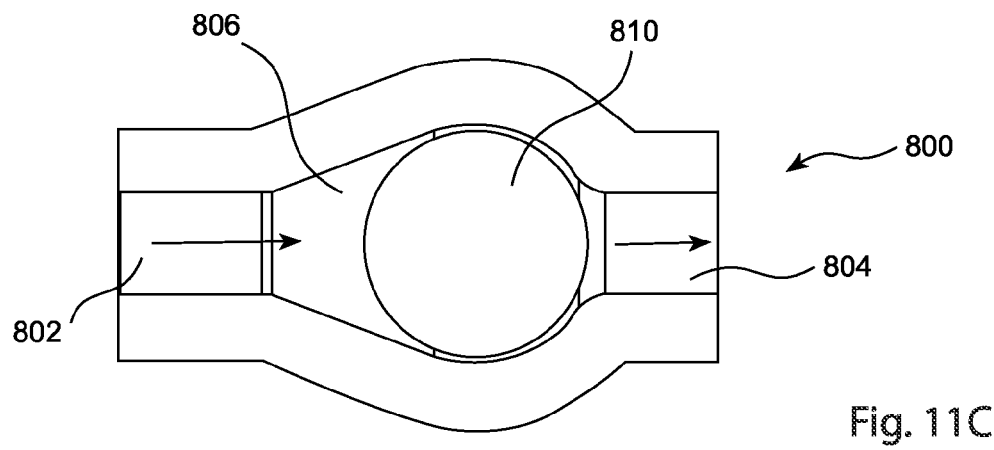

Referring now to FIGS. 11A to 11C, these show another embodiment of holder 800 having similar characteristics to the previously described embodiments and is depicted in schematic form in these Figures. The primary difference between the holder 800 and the holder 700 of FIGS. 9A to 10 is that the internal chamber 806 of the holder 800 is non-spherical, instead having a tapering shape towards the inlet 802, while being generally spherical at its end close to the outlet 804. Such a shape, it has been found, assists the flow of driving fluid through the chamber 806 and thus in the pulling of filamentary material of the carrier 810 and into the delivery catheter.

Referring now to FIGS. 12A to 12C, these show in schematic form a catheter 12 in transverse cross-section with one or more filaments of bioabsorbable material 24 held therein. The current goal of the device is to introduce bioabsorbable material in the form of a filament into the cavity of an aneurysm. It is postulated that the material will initially create an embolic reaction within the cavity of the aneurysm, before acting as a scaffold to engender cellular growth. The filament 24 itself is constrained in size to fit within the lumen of the catheter 12 to enable delivery. When coming into contact with the blood, cells will permeate the material 24 and the expectation is that the material will remodel over time into natural tissue. If sized correctly, it is possible to introduce more than one filament at the same time through the lumen of the catheter 12. The introduction of multi-filaments instead of a single filament, as shown in FIGS. 12B and 12C would aid the following:

1) increased contact (surface area) between the filament and the blood to aid thrombogenicity;

2) slight separation of the filaments upon exiting the aneurysm may help distribute the material evenly;

3) less fluid required to deliver the filament in longer lengths, albeit in smaller volumes.

The delivery systems taught herein functions when a fluid is introduced within the catheter 12 dragging the filament 24 along its lumen. A small but minimum fluid velocity is required to generate enough friction to drag the filament 24, thereby making the applied force by the user (for example with a syringe) a relevant element in its operation. While no patient risk is perceived by applying a force too small to enable the system to work, the function of the pressure valve will enhance the system as:

1) it will prevent the user from introducing excess liquid into the aneurysm without any advancement of the material;

2) it will provide tactile feedback to the user as the valve will prevent liquid from exiting the syringe without the application of a minimum force, giving the user 'feel' when operating the device.

An example of a minimum pressure valve arrangement is shown in FIGS. 13A to 15B, in which it can be seen that a valve 55 is disposed at the inlet to the receptacle 30. The valve 55 itself can be made from any suitable material, such as a polymer or rubber. Silicone is a particularly suitable material due to its mechanical properties.

As depicted in the Figures, the optimal shape of the valve 55 is a dome which is split into a number of leaves or elements 57 (four leaves in this example), and a disc 59 at the base which functions as an anchor to fix the valve 55 within the receptacle 30.

Figure 13A:
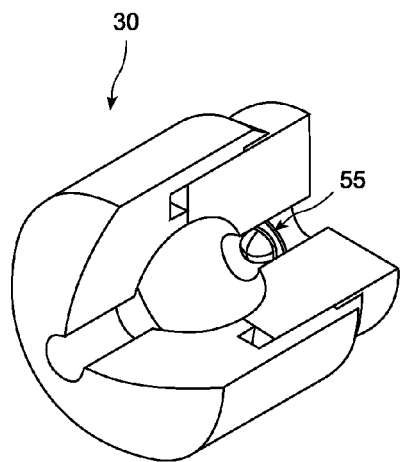
FIGS. 13A and 13B are perspective views of an example of receptacle including a minimum fluid pressure valve.
Figure 13B:
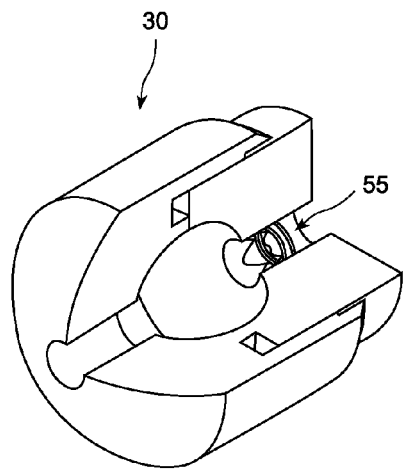
Figure 14A:
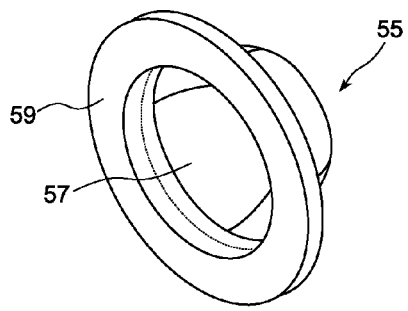
FIGS. 14A and 14B are perspective views of the valve in FIGS. 13A and 13B in a closed condition.
Figure 14B:
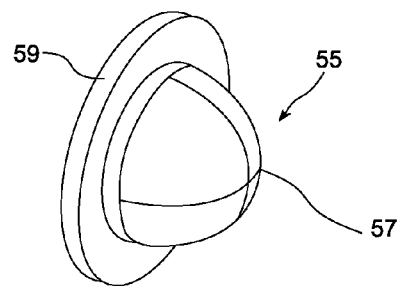
Figure 15A:
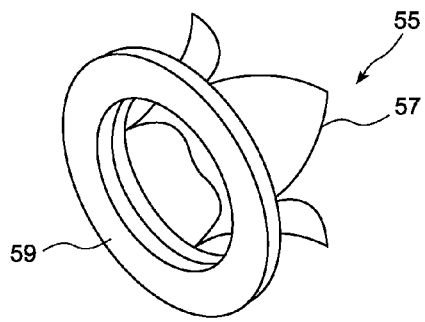
FIGS. 15A and 15B are perspective views of the valve in FIGS. 13A and 13B in an open condition.
Figure 15B:
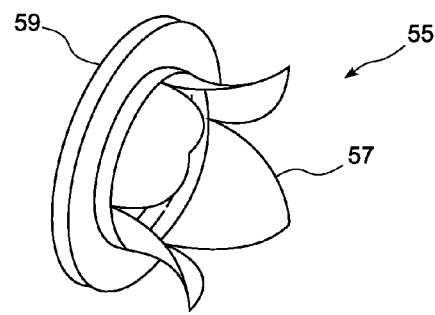

FIGS. 13B, 15A and 15B show the valve 55 when sufficient fluid force is applied. The capacity of the valve 55 to open will be determined by the choice of material and wall thickness. The valve 55 will return to its natural closed position, as seen in FIGS. 13A, 14A and 14B, when the force applied (by the syringe) becomes too small to keep the leaves 57 open.

The valve 55 is preferably positioned at the proximal end of the receptacle, between the syringe connection and the main chamber. However, in other embodiments the valve could be positioned at the distal end of the receptacle, within the driving fluid supply or even in the tubular delivery element. There may be provided more than one valve.

In the embodiment shown, the valve 55 is domed.

Although the embodiments described above use a delivery catheter, the apparatus could delivery filamentary material through any suitable tubular delivery device. The examples include a cannula or needle.

It is not excluded that the carrier could be at least partially cylindrical and of floating or suspended form.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

What is claimed:

1. Apparatus for delivering filamentary material into a patient including:
    a tubular delivery element having a proximal end, a distal end and a lumen extending within the tubular delivery element from the proximal to the distal ends;
    a material dispenser coupled at the proximal end of the tubular delivery element, the material dispenser including a receptacle having an internal wall of which at least a part has a generally rounded shape, the receptacle including an aperture for receiving driving fluid into the receptacle and an outlet coupled to the lumen of the tubular delivery element; and
    a material carrier operable to carry a length of filamentary material, the material carrier having a generally rounded shape conforming at least to said rounded part of the internal wall of the receptacle and having a size smaller than a size of the receptacle;
    the filamentary material being wound around the carrier and having an end located through the outlet for feeding into and through the lumen of the tubular delivery element, wherein the carrier is free to rotate in any direction within the receptacle.

2. Apparatus according to claim 1, wherein the tubular delivery element includes at least one of a catheter, a cannula and a needle.

3. Apparatus according to claim 1, wherein the carrier has a generally spherical shape.

4. Apparatus according to claim 1, wherein the carrier has a generally ovoidal shape.

5. Apparatus according to claim 1, wherein the carrier includes at least one groove extending therearound, the filamentary material being retained in the groove.

6. Apparatus according to claim 5, wherein the at least one groove is disposed at or adjacent a point of greatest diameter or perimeter of the carrier.

7. Apparatus according to claim 5, including a plurality of grooves.

8. Apparatus according to claim 7, wherein the grooves lie in generally parallel planes relative to one another.

9. Apparatus according to claim 7, wherein at least two of the grooves lie in planes which cross one another.

10. Apparatus according to claim 1, wherein the carrier is made of a plastics material.

11. Apparatus according to claim 1, wherein the carrier includes a hollow core.

12. Apparatus according to claim 1, wherein the carrier is made of a material buoyant in water or a water based solution.

13. Apparatus according to claim 1, wherein the carrier is uncoupled from the receptacle.

14. Apparatus according to claim 1, wherein the carrier becomes suspended in driving fluid when said driving fluid is fed into the receptacle of the material dispenser.

15. Apparatus according to claim 1, wherein the receptacle is at least partially transparent or translucent.

16. Apparatus according to claim 1, wherein substantially the entirety of the receptacle is transparent or translucent.

17. Apparatus according to claim 1, including a fluid supply and pump for pumping driving fluid into the receptacle.

18. Apparatus according to claim 17, wherein the pump includes a syringe.

19. Apparatus according to claim 1, wherein the material is SIS, polysaccharide, a biocompatible polymeric thread or other biocompatible material.

20. Apparatus for delivering filamentary material into a patient, including a receptacle provided with an internal chamber for holding filamentary material, an aperture for receiving driving fluid into the chamber, an outlet through which filamentary material can pass from the chamber a material carrier operable to carry the filamentary material and is free to rotate in any direction within the receptacle, and a pressure sensitive valve associated with the receptacle, the pressure sensitive valve being closed when the pressure of driving fluid is below a threshold and open when the pressure of driving fluid is above the threshold, the pressure sensitive valve when open allowing fluid flow through the chamber and dispensation of filamentary material from the outlet.

21. Apparatus according to claim 20, wherein the pressure sensitive valve is disposed at least one of the inlet and the outlet.

22. Apparatus according to claim 21, wherein the valve is located at the inlet.

23. Apparatus according to claim 20, wherein the valve includes at least one resilient valve leaf deformable when fluid pressure thereon exceeds the threshold.

24. Apparatus according to claim 20, wherein the valve is domed to provide one-way fluid flow therethrough.

25. Apparatus according to claim 20, including filamentary material disposed in the receptacle.

* * * * *